United States Patent [19]
Fedouloff et al.

[11] Patent Number: 6,100,397
[45] Date of Patent: Aug. 8, 2000

[54] PROCESS FOR THE PREPARATION OF N-[(1-$^N$BUTYL-4-PIPERIDYL)METHYL]-3,4-DIHYDRO-2H-[1,3]OXAZINO[3,2-A] INDOLE-10-CARBOXAMIDE AND SALTS AND INTERMEDIATES IN THE PROCESS

[75] Inventors: Michael Fedouloff, Acton; Gillian Elizabeth Smith, Bishops Stortford; David William Guest, Harlow; John Bryce Strachan, Bishops Stortford, all of United Kingdom

[73] Assignee: Smithkline Beecham plc, Brentford, United Kingdom

[21] Appl. No.: 09/242,413

[22] PCT Filed: Aug. 11, 1997

[86] PCT No.: PCT/US97/04413

§ 371 Date: Feb. 16, 1999

§ 102(e) Date: Feb. 16, 1999

[87] PCT Pub. No.: WO98/07728

PCT Pub. Date: Feb. 26, 1998

[30]    Foreign Application Priority Data

Aug. 16, 1996 [GB] United Kingdom ............... 9617188
Sep. 11, 1996 [GB] United Kingdom ............... 9618968

[51] Int. Cl.$^7$ .................. C07D 265/12; C07D 209/34
[52] U.S. Cl. .................. 544/89; 544/89; 548/486
[58] Field of Search .................. 544/89; 548/486

[56]    References Cited

U.S. PATENT DOCUMENTS 5,705,498  1/1998  Gaster et al. ............... 514/230.2

FOREIGN PATENT DOCUMENTS

WO 93/18036  9/1993  WIPO .

OTHER PUBLICATIONS

Faster, et al. J. Med. Chem., 1995, 38, pp. 4760–4763.

Wayman, et al., Bioorganic & Medicinal Chemistry vol. 4, No. 2, 1996, pp. 255–260.

*Primary Examiner*—Richard L. Raymond
*Assistant Examiner*—Ben Schroeder
*Attorney, Agent, or Firm*—Soma G. Simon; William T. King; Charles M. Kinzig

[57]    ABSTRACT

A process for the preparation of SB 207266 or a pharmaceutically acceptable salt thereof, which process comprises the reaction of N-(1-$^n$butyl-4-piperidyl)methylamine with a compound of formula (A),

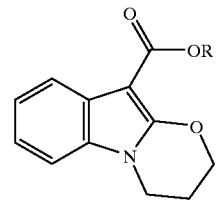

(A)

wherein R is alkyl.

7 Claims, No Drawings

PROCESS FOR THE PREPARATION OF N-[(1-$^N$BUTYL-4-PIPERIDYL)METHYL]-3,4-DIHYDRO-2H-[1,3] OXAZINO[3,2-A] INDOLE-10-CARBOXAMIDE AND SALTS AND INTERMEDIATES IN THE PROCESS

This invention relates to a new synthetic process to a compound having pharmacological activity.

WO93/18036 (SmithKline Beecham plc) describes compounds having 5-HT$_4$ receptor antagonist activity of formula (I), or a pharmaceutically acceptable salt thereof:

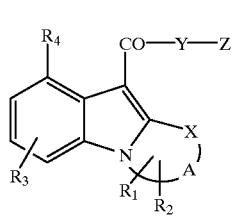

wherein

X is O, S, SO, SO$_2$, CH$_2$, CH or NR wherein R is hydrogen or C$_{1-6}$ alkyl;

A is a saturated or unsaturated polymethylene chain of 2–4 carbon atoms;

R$_1$ and R$_2$ are hydrogen or C$_{1-6}$ alkyl;

R$_3$ is hydrogen, halo, C$_{1-6}$ alkyl, amino, nitro or C$_{1-6}$ alkyl;

R$_4$ is hydrogen, halo, C$_{1-6}$ alkyl or C$_{1-6}$ alkoxy;

Y is O or NH;

Z is of sub-formula (a), (b) or (c):

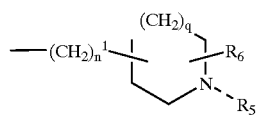

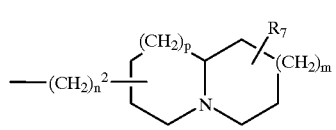

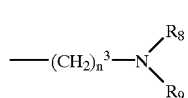

wherein $n^1$ is 1, 2, 3 or 4; $n^2$ is 0, 1, 2, 3 or 4; $n^3$ is 2, 3, 4 or 5;

q is 0, 1, 2 or 3; p is 0, 1 or 2; m is 0, 1, or 2;

R$_5$ is hydrogen, C$_{1-12}$ alkyl, aralkyl or R$_5$ is (CH$_2$)$_z$-R$_{10}$ wherein z is 2 or 3 and R$_{10}$ is selected from cyano, hydroxyl, C$_{1-6}$ alkoxy, phenoxy, C(O)C$_{1-6}$ alkoxy, COC$_6$H$_5$, -CONR$_{11}$R$_{12}$, NR$_{11}$COR$_{12}$, SO$_2$NR$_{11}$R$_{12}$ or NR$_{11}$SO$_2$R$_{12}$ wherein R$_{11}$ and R$_{12}$ are hydrogen or C$_{1-6}$ alkyl; and R$_6$, R$_7$ and R$_8$ are independently hydrogen or C$_{1-6}$ alkyl; and R$_9$ is hydrogen or C$_{1-10}$ alkyl;

or a compound of formula (I) wherein the CO-Y linkage is replaced by a heterocyclic bioisostere;

having 5-HT$_4$ receptor antagonist activity.

Examples of alkyl or alkyl containing groups described herein include C$_1$, C$_2$, C$_3$, C$_4$, C$_5$, C$_6$, C$_7$, C$_8$, C$_9$, C$_{10}$, C$_{11}$ or C$_{12}$ branched, straight or cyclic alkyl, as appropriate. C$_{1-4}$ alkyl groups include methyl, ethyl, n- and iso-propyl, n-, iso-, sec- and tert-butyl. Cyclic alkyl includes cyclopropyl, cyclobutyl, cyclopentyl, cyclohexyl, cycloheptyl and cyclooctyl.

The pharmaceutically acceptable salts of the compounds of the formula (I) include acid addition salts with conventional acids such as hydrochloric, hydrobromic, boric, phosphoric, sulfuric acids and pharmaceutically acceptable organic acids such as acetic, tartaric, maleic, citric, succinic, benzoic, ascorbic, methanesulfonic, α-keto glutaric, α-glycerophosphoric, and glucose-1-phosphoric acids.

Examples of pharmaceutically acceptable salts include quaternary derivatives of the compounds of formula (I) such as the compounds quaternised by compounds R$_x$-T wherein R$_x$ is C$_{1-6}$ alkyl, phenyl-C$_{1-6}$ alkyl or C$_{5-7}$ cycloalkyl, and T is a radical corresponding to an anion of an acid. Suitable examples of R$_x$ include methyl, ethyl and n- and iso-propyl; and benzyl and phenethyl. Suitable examples of T include halide such as chloride, bromide and iodide.

Examples of pharmaceutically acceptable salts also include internal salts such as N-oxides.

The compounds of the formula (I), their pharmaceutically acceptable salts, (including quaternary derivatives and N-oxides) may also form pharmaceutically acceptable solvates, such as hydrates, which are included wherever a compound of formula (I) or a salt thereof is referred to.

Example 3 describes the hydrochoride salt of the compound of formula (I):

A is —CH$_2$—(CH2)$_r$—CH$_2$— wherein r is 1;

R$_1$ and R$_2$ are hydrogen;

R$_3$ is hydrogen;

R$_4$ is hydrogen;

Y is NH; and

Z is of sub-formula (a), and is of structure (i):

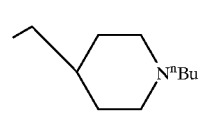

This compound is N-[(1-$^n$butyl4-piperidyl)methyl]-3,4-dihydro-2H-[1,3]oxazino[3,2-a]indole-10-carboxamide SB 207266, (the hydrochloride salt is SB 207266-A) which is being developed by SmithKline Beecham plc as the active ingredient in a medicament for treatment of irritable bowel syndrome.

Example 3 of WO93/18036 describes a method of preparation of SB 207266-A from N-[(1-$^n$butyl4-piperidyl)methyl]indole-3-carboxamide (i.e. the compound corresponding to SB 207266, without the oxazino moiety), by reacting with N-chlorosuccinimide and 3-bromo-1-propanol, followed by treatment with sodium carbonate. N-[(1-$^n$butyl-4-piperidyl)methyl]indole-3-carboxamide is prepared by coupling N-(1-$^n$butyl-4-piperidyl)methylamine with a indole-3-carboxylic acid.

An alternative process for preparing SB 207266-A has now been discovered which involves the use of the N-(1-$^n$butyl4-piperidyl)methylamine intermediate at a later stage in the process thus resulting in an increased yield of SB 207266-A relative to the amount of this intermediate, which is relatively expensive to produce.

Accordingly, the present invention provides a process for the preparation of SB 207266 or a pharmaceutically acceptable salt thereof, which process comprises the reaction of of N-(1-"butyl-4-piperidyl)methylamine with a compound of formula (A):

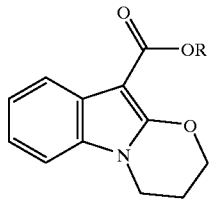

(A)

wherein R is alkyl, such as methyl or ethyl.

The compound of formula (A) wherein R is methyl is methyl 3,4-dihydro-2H-[1,3]-oxazino[3,2-a]indole-10-carboxylate.

The conditions and reagents for this reaction are similar to those described in the literature. A mixture of the amine and ester in a suitable solvent (eg toluene) is treated with a solution of trimethylaluminum in toluene or hexanes at ambient temperature. The resulting solution is then heated, preferably to reflux (112° C.) for about four hours until the reaction is complete. The reaction is cooled to about 70° C. and quenched by cautious addition of aqueous sodium hydroxide solution. The aqueous layer is separated and the mixture washed once more with caustic and twice with water maintaining the temperature at about 70° C. The product is isolated as described in the attached Example.

Alternative catalysts include $NaH_2Et_2Al$ which is used in a similar way to $AlMe_3$.

BuLi is also suitable but is used at lower temperatures and requires two equivalents of the base and two equivalents of the amine.

The mechanism of the reaction and role of the aluminum or lithium based catalyst is discussed in the references listed below:

Use of $AlMe_3$: Anwer Basha, Michael Lipton and Steven M. Weinreb, Tetrahedron Letters, 48, 4171, 1977.
Use of $NaH_2Et_2Al$: Tae Bo Sim and Nung Min Yoon, Synlett., 1994, 827
Use of BuLi: Kim-Wen n Yang, Joseph, G. Cannon and John G. Rose,
Tetrahedron Letters, 21, 1791, 1970

The oxazinoindole compound of the formula (A) is prepared from the corresponding indole by reaction with N-chlorosuccinimide and a 3-halo-propanol, such as 3-chloropropane or 3-bromopropanol followed by cyclisation of the intermediate (B) by treatment with base in a suitable solvent.

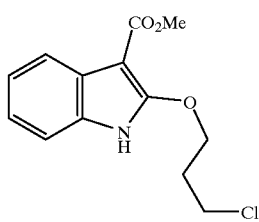

Suitable solvents for the cyclisation include acetone and toluene, and suitable bases include potassium carbonate, aqueous sodium hydroxide.

The use of aqueous sodium hydroxide solution, even at 80° C. does not cause any significant hydrolysis of the ester.

In the case of toluene/aqueous sodium hydroxide, a phase transfer catalyst (eg tetrabutylammonium bromide) may be added, resulting in accelerating the reaction and allowing it to proceed at a lower temperature.

The intermediate (B) may either be used as a crude oil or isolated as a white crystalline solid and then cyclised in quantitative yield to give a solution of (A) in a suitable solvent (eg toluene) for coupling with the amine.

Compounds of the formula (A) and (B) are novel and form an aspect of the invention.

The following Example illustrates the invention. The following Description illustrates the preparation of an intermediate of formula (A).

EXAMPLE i) Preparation of N-[(1-butyl-4-piperidinyl)methyl]-3,4-dihydro-2H-[1,3]-oxazino[3,2-a]indole-10-carboxamide [SB-207266]

Method A Toluene (85L) was azeotropically dried in an argon purged reactor, cooled to 10° C. and a solution of trimethylaluminum in toluene (18.57 kg, 16.7% w/w, 43 mole) added. To this at 20 to 24° C. was added a solution of 1-n-butyl-4-piperidinylmethylamine (7.39 kg, 99.4% pure, 42.7 mole) in toluene (22 L) over 43 minutes. Methyl 3,4-dihydro-2H-[1,3]-oxazino[3,2-a]indole-10-carboxylate (9.65 kg, 98.9% pure, 41.3 mole) was added in one portion and the reaction heated to reflux at 112° C. for 4 hours 10 minutes after which time the reaction was judged to be complete by HPLC analysis. 10% Sodium hydroxide solution (52.2 L), prepared from 32% ww sodium hydroxide (24 L) and water (80 L), was added cautiously over 16 minutes at about 60 to 70° C. The resulting mixture was heated to 70 to 80° C. and the aqueous layer separated. The toluene layer was washed with 10% sodium hydroxide (52.2 L) followed twice by water (29 L each wash). The toluene layer was cooled and diluted with hexane fraction (133 L) to crystallise the product. After cooling to about 2° C. overnight the product was collected by filtration, washed on the filter with hexane (21 L) and dried in vacuo at 40° C. overnight to give SB-207266 batch 207266-HP8 (12.26 kg, 94.5% pure, 75.9%).

Method B 1.6M Butyllithium in hexane (1.4 ml) was added to toluene (2 ml) at −10°. A solution of 1-n-butyl-4-piperidinyimethylamine (0.38 g) in toluene (3 ml) was added and the mixture was stirred for 5 mins. A solution of methyl 3,4-dihydro-2H-[1,3]-oxazino[3,2-a]indole-10-carboxylate (0.23 g) in hot toluene (5ml) was added and the mixture was stirred at −10° for 5 mins. The mixture was diluted to 1000 ml with acetonitrile:water and relative assay of the solution showed an SB-207266 content of 343mg (93% yield).

Method C A mixture of methyl 2-(3-chloropropoxy)-indole-3-carboxylate (100 g, 0.37 mol), aqueous sodium hydroxide solution (38 ml, 10.8M, 0.41 mol), water (38 ml) and tetrabutylammonium bromide (6.0 g, 0.019 mol) in toluene (1000 ml) was stirred at 50–60° C. for about one hour. Water (120 ml) was added and the aqueous layer was removed. The organic layer was washed with water (120 ml) and dried by azeotropic distillation of toluene (250 m) giving a dry solution of methyl 3,4-dihydro-2H-[1,3]-oxazino[3,2-a]indole-10-carboxylate in toluene. This solution was cooled to ambient temperature and treated sequentially with a solution of 1-butyl-4-piperidinylmethylamine (66.8 g, 0.39 mol) in toluene (200 ml) followed by a solution of trimethylaluminium in toluene (196 ml, 2.0M, 0.39 mol). The mixture was heated to reflux and stirred for three hours.

The reaction was quenched by cautious addition of aqueous sodium hydroxide solution (460 ml, 10% w/v) and then washed once with aqueous sodium hydroxide solution (460 ml, 10% w/v) and twice with water (275 ml each wash) while maintaining the temperature at about 70° C. Toluene (200 ml) was added and the resulting solution was dried by azeotropic distillation of toluene (200 ml) at about 55° C. under reduced pressure. Hexane (1400 ml) was added and the resulting slurry cooled to about 0–5° C. for about one hour. The solid was isolated by filtration and dried in vacuo to give the product, N-[(1-butyl-4-piperidinyl)methyl]-3,4-dihydro-2H-[1,3]-oxazino[3,2-a]indole-10-carboxamide, (114.7 g, 83%) as a white crystalline solid.

ii) Preparation of N-[(1-butyl4-piperidinyl)methyl]-3,4-dihydro-2H-[1,3]-oxazino[3,2-a]indole-10-carboxamide hydrochloride [SB-207266-A]

Method A N-[(1-Butyl-4-piperidinyl)methyl]-3,4-dihydro-2H-[1,3]-oxazino[3.2-a]indole-10-carboxamide (SB-207266) (12.26 kg 94.5% pure. 31.35 moles) was dissolved in acetone (70.5 L) at 41° C. Anhydrous HCl in propan-2-ol (8.98 L, 3.86 molar, 34.7 moles), made by dissolving HCl gas (3.1 kg) in propan-2-ol (20 L), was added over 8 minutes allowing the temperature to rise to 57° C. The mixture was cooled to 4° C. and stirred at 2 to 4° C. for 2 hours. The precipitate was filtered off washed with cold acetone (25 L) and dried at atmospheric pressure at 40 to 50° C. for 17 hours to give the crude product as a white solid (12.94 kg; 96.1%).

The crude product (12.94 kg) was dissolved in hot ethanol (107 L) and filtered through celite, washing the filter bed with further hot ethanol (18 L). The filtrate was heated to 75° C. and hot filtered hexane (68 L) was added. The mixture was cooled to 19° C. over about 4 hours and then to 4° C. and stirred overnight at 1° C. The white solid was filtered off, washed with a 1:1 mixture of cold ethanol/hexane (27 L) and dried in vacuo at 50° C. for 23 hours to give SB-207266A (12.36 kg, 96.2% from SB-207266). This was milled in an Apex Comminuting mill through a 0.125 inch×0.125 inch square mesh at medium speed and with hammers forward. 12.3 kg (95.8% from SB-207266) was isolated as a fine, homogeneous white powder.

Method B N-[(1-Butyl-4-piperidinyl)methyl]-3,4-dihydro-2H-[1,3]-oxazino[3,2-a]indole-10-carboxamide (SB-207266) (100 g, 0.27 mol) was dissolved in ethanol (870 ml) and the resulting solution filtered to remove particulates. Anhydrous HCl in ethanol (83 ml, 3.6M, 0.30 mol) was added causing the product to precipitate out of solution. The slurry was heated to redissolve the solid and hexane (550 ml) was added. After cooling to room temperature, the mixture was cooled to 0–5° C. and stirred at that temperature for about two hours. The solid was isolated by filtration and dried in vacuo at about 40° C. to give the product, N-[(1-butyl-4-piperidinyl)methyl]-3,4-dihydro-2H-[1,3]-oxazino [3,2-a]indole-10-carboxamide hydrochloride, (102.8 g) in 94% yield.

DESCRIPTION

Preparation of methyl-3,4 dihydro-2H-[1,3]-oxazino[3,2-a]indole-10-carboxylate

Method A A solution of 3-chloropropanol (14.74 kg, 98.4% pure, 153.4 mole) in dichloromethane (67 L) was cooled to -17° C. In a second vessel dichloromethane (68 L), methyl indole-3-carboxylate (13.5 kg, 99.8% pure, 76.9 mole) and 1,4-diazabicyclo[2.2.2]octane (4.75 kg, assumed 100% pure, 42.3 mole) were cooled to 0° C. N-Clorosuccinimide (11.3 kg, 99.5% pure, 84.2 mole) was added to the second vessel and stirred at 0° C. for 10 minutes. In the meantime methane sulphonic acid (0.59 L, 99.7% pure, 6.14 mole) was added to the first vessel. The solution in the second vessel was added to the first vessel over 49 minutes at -15 to 3° C. and the resulting mixture stirred for a further 31 minutes at -5 to 0° C. 10% Sodium carbonate solution (147 L), made from sodium carbonate (42.2 kg, 398 mole) and process water (422 L), was added over 14 minutes and stirred. The organic layer was separated and washed twice with 10% sodium carbonate solution (147 L each wash). The organic layer was dried over anhydrous sodium sulphate, filtered and concentrated under reduced pressure below 30° C. The concentrate was dissolved in acetone (101 L) at about 18° C. and potassium carbonate (14.9 kg) added. The mixture was stirred at 18 to 28° C. for 18 hours. Analysis of the reaction showed it to be complete. The inorganic salts were filtered off, the filtrate concentrated under reduced pressure below 30° C. and dissolved in dichloromethane (101 L). The dichloromethane solution was washed twice with 5% sodium bicarbonate solution (85 L each wash), made from sodium bicarbonate (8.3 kg) and water (167 L) and dried over anhydrous sodium sulfate. After filtration the filtrate was concentrated under reduced pressure to a base temperature of about 95° C. and diluted with toluene (12 L). The toluene solution was cooled, causing the product to crystallise and cooling continued to about 0° C. overnight. The product was collected by filtration, washed on the filter with cold (0° C.) toluene (7 L) and dried in vacuo at 30° C. for 21 hours to give the title compound (9.654 kg, 98.9% pure, 53.7%).

Method B A solution of 3-chloropropanol (142.47 g, 1.51 mole) in dichloromethane (1200 ml) was cooled to -20° C. In a second vessel dichloromethane (1300 ml), methyl indole-3-carboxylate (240.0 g, 1.37 mole) and 1,4-diazabicyclo[2.2.2]octane (84.52 g 0.75 mole) were cooled to 0° C. N-Chlorosuccinimide (201.22 g 1.51 mole) was added to the second vessel and stirred at 0° C. for 10 minutes. In the meantime methane sulphonic acid (10.56 ml) was added to the first vessel. The solution in the second vessel was added to the first vessel keeping the temperature below about 0° C., and the resulting mixture stirred for a further 2.5 hours at -5 to 0° C. 10% Sodium carbonate solution (2500 ml) was added and stirred. The organic layer was separated and washed twice with 10% sodium carbonate solution (2500 ml each wash). The organic layer was dried over anhydrous sodium sulfate, filtered and concentrated under reduced pressure. The concentrate was triturated with ethyl acetate (120 ml) and the mixture stirred at 0° C. for about 1 hour. The resulting solid was filtered, washed a small quantity of ethyl acetate and dried under vacuum to give methyl 2-(3-chloropropoxy)-indole-3-carboxylate (202.5 g) as a white crystalline solid in 55% yield.

A mixture of methyl 2-(3-chloropropoxy)-indole-3-carboxylate (81.5 g, 0.304 mole), aqueous sodium hydroxide solution (3 ml, 10.8M, 0.335 mole), water (31 ml) and tetrabutylammonium bromide (4.9 g, 0.015 mole) in toluene (815 ml ) was stirred at 50–60° C. for about 45 minutes. The aqueous layer was removed and the organic layer washed twice with water (100 ml each wash). The resulting toluene solution was dried by azeotropic distillation of solvent (265 ml ) under reduced pressure (60° C., 160 mbar) giving a dried solution of the title compound in toluene.

Method C A solution of 3-chloropropanol (142.47 g, 1.51 mol) in dichloromethane (1200ml) was cooled to -20° C. In a second vessel dichloromethane (1300 ml), methyl indole-3-carboxylate (240.0 g, 1.37 mol) and 1,4-diazabicyclo [2.2.2]octane (84.52 g 0.75 mol) were cooled to 0° C. N-Chlorosuccinimide (201.22 g 1.51 mole) was added to the second vessel and stirred at 0° C. for 10 minutes. In the meantime methane sulfonic acid (10.56 ml) was added to the first vessel. The solution in the second vessel was added to the first vessel keeping the temperature below about 0° C., and the resulting mixture stirred for a further 2.5 hours at −5 to 0° C. 10% Sodium carbonate solution (1250 ml) was added and the mixture stirred for about 30 minutes. The organic layer was separated and washed once more with 10% sodium carbonate solution (1250 ml) and once with water (1250 ml). The organic layer was dried over anhydrous sodium sulfate, filtered and concentrated under reduced pressure. The concentrate was triturated with toluene (400 ml) and the mixture stirred at 0° C. for about 1 hour. The resulting solid was filtered, washed with toluene and dried in vacuo to give methyl 2-(3-chloropropoxy)-indole-3-carboxylate (245.5 g) as a white crystalline solid in 67% yield.

What is claimed is:

1. A process for the preparation of N-[(1-n-butyl-4-piperidyl)methyl]-3,4-dihydro-2H-[1,3]oxazino[3,2-a]indole-10-carboxamide or a pharmaceutically acceptable salt thereof, which process comprises the reaction of of N-(1-"butyl-4-piperidyl)methylamine with a compound of formula (A):

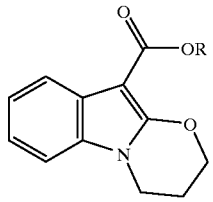

(A)

wherein R is alkyl.

2. A process according to claim 1 wherein R is methyl or ethyl.

3. A process according to claim 1 wherein the reaction is catalysed by a aluminum or lithium based catalyst.

4. A process according to claim 3 wherein the catalyst is trimethylaluminum.

5. A compound of formula (A):

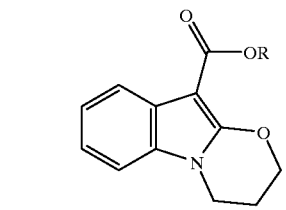

wherein R is alkyl.

6. Methyl-3,4 dihydro-2H-[1,3]-oxazino[3,2-a]indole-10-carboxylate.

7. A compound of formula (B):

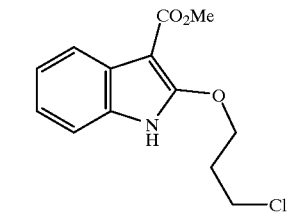

(B)

Processes for the preparation of N-[(1-nbutyl-4-piperidyl)methyl]-3,4-dihydro-2H-[1,3]oxazino[3,2-A]indole-10-carboxamide and its salts are provided.

* * * * *

UNITED STATES PATENT AND TRADEMARK OFFICE
CERTIFICATE OF CORRECTION

PATENT NO.    : 6,100,397
DATED         : August 8, 2000
INVENTOR(S)   : Michael Fedouloff, Gillian Elizabeth Smith, David William Guest and John Bryce Strachan It is certified that error appears in the above-identified patent and that said Letters Patent is hereby corrected as shown below:

Title page,
Item [86], PCT No.: "PCT/US97/04413" should be -- PCT/EP97/04413 --

Column 8,
Lines 33-35, please delete "Processes for the preparation of N-[(1-nbutyl-4-piperidyl)methyl]-3,4-dihydro2H-[1,3]oxazino[3,2-A]indole-10-carboxamide and its salts are provided," and insert -- . -- (a period) therefor.

Signed and Sealed this

Ninth Day of July, 2002

Attest:

Attesting Officer

JAMES E. ROGAN
Director of the United States Patent and Trademark Office